United States Patent [19]

Day

[11] 4,110,373
[45] Aug. 29, 1978

[54] PROCESS FOR THE PREPARATION OF BENZOYL HALIDE AND HALOSULFONYLBENZOYL HALIDE

[75] Inventor: F. Howard Day, Grand Island, N.Y.

[73] Assignee: Hooker Chemicals & Plastics Corp., Niagara Falls, N.Y.

[21] Appl. No.: 839,045

[22] Filed: Oct. 3, 1977

[51] Int. Cl.$^2$ .................. C07C 51/58; C07C 63/10; C07C 143/38; C07C 143/40
[52] U.S. Cl. .................. 260/543 R; 260/544 D
[58] Field of Search .................. 260/543 R, 544 D

[56] References Cited

U.S. PATENT DOCUMENTS 3,290,370  12/1966  Weil et al. ................. 260/544
3,322,822  5/1967   Gelfand ..................... 260/544

OTHER PUBLICATIONS

Chemical Abstracts, vol. 29, column 5090$^2$ (1935).

Primary Examiner—Gerald A. Schwartz

Attorney, Agent, or Firm—Peter F. Casella; William J. Crossetta, Jr.; Arthur S. Cookfair

[57] ABSTRACT

A process for the preparation of benzoyl halide and meta-halosulfonyl benzoyl halide comprises adding to oleum and reacting therewith a benzotrihalide compound characterized by the formula:

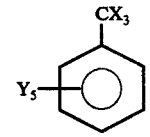

wherein X is bromine or chlorine and Y is individually selected from the group consisting of fluorine, chlorine, bromine, iodine, alkyl, preferably of one to six carbon atoms, halosubstituted alkyl, preferably trichloromethyl or tribromomethyl, aryl, preferably phenyl, and hydrogen, with the proviso that at least one Y substituent at a meta position is hydrogen.

11 Claims, No Drawings

PROCESS FOR THE PREPARATION OF BENZOYL HALIDE AND HALOSULFONYLBENZOYL HALIDE

BACKGROUND OF THE INVENTION

This invention relates to an improved process for the preparation of benzoyl halides and meta-halosulfonylbenzoyl halides and, more particularly, to such process involving the reaction of benzotrihalide with oleum.

Benzoyl halides and chlorosulfonylbenzoyl halides are well known in the chemical industry and have been employed in as intermediates for a variety of known and useful end products. Benzoyl halides, are highly reactive acid halides, useful in a variety of reactions to introduce the benzoyl group into organic compounds, especially through Friedel-Crafts reactions. Benzoyl halides are employed in the preparation of perfumes, pharmaceuticals, dyes, resins and pesticides. Similarly, halosulfonylbenzoyl halides are known to be useful for a variety of purposes and have been employed, for example, as polymerization catalysts and as intermediates in the preparation of pharmaceuticals and azo dyes. In addition, meta-halosulfonylbenzoyl halides, may be desulfonylated in a known manner to prepare m-halobenzoyl halides, which, in turn, are useful for various purposes in the chemical industry, including, for example, as chemical intermediates for the preparation of dyes; pharmaceuticals; agricultural chemicals; as well as various other organic chemical end products.

Various methods for the preparation of benzoyl halides or meta-sulfonylbenzoyl halides are known in the art. It is known, for example, from U.S. Pat. No. 3,691,217, that benzoyl chlorides and benzaldehydes may be produced by reacting benzo polychloromethanes, such as benzotrichloride, with an organic carboxylic acid in the presence of a tin chloride catalyst.

U.S. Pat. No. 3,290,370, to Weil and Lisanke, disclose the preparation of m-chlorosulfonylbenzoyl chloride by reaction of benzotrichloride with chlorosulfonic acid. The stoichiometry of the reaction is such that, even under ideal conditions, for each mole of desired product, two moles of mineral acid are produced, with the need for disposal thereof. In addition, to obtain high yields of the desired m-chlorosulfonylbenzoyl chloride, substantial excess of the chlorosulfonic acid is employed, presenting additional problems of separation, and disposal or recycling thereof.

U.S. Pat. No. 3,322,822 to Gelfand, discloses the preparation of m-chlorosulfonylbenzoyl chloride by reaction of benzotrichloride and sulfur trioxide. With the use of substantial excess of sulfur trioxide reactant, yields of m-chlorosulfonylbenzoyl chloride as high as 65% are shown to be obtainable.

Although the prior art provides a variety of processes for the preparation of either benzoyl halides or halobenzoylsulfonyl halides, it will be appreciated that still further improvements in efficient utilization of reactants is desirable as well as improvements in the yield of the meta-isomer of halosulfonylbenzoyl halide obtainable. Accordingly, it is an object of this invention to provide an improved process for the preparation of halosulfonylbenzoyl halides wherein the meta-isomer thereof may be selectively produced in high yields. It is a further object to provide a process for the preparation of co-products, benzoyl halides and halosulfonylbenzoyl halides wherein the proportional yield of each may be controllably varied.

SUMMARY OF THE INVENTION

This invention provides a process for the co-production of benzoyl halides and m-halosulfonylbenzoyl halides by reaction of oleum with a benzotrihalide compound of the formula:

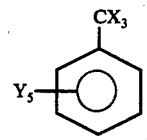

wherein X is bromine or chlorine and Y is individually selected from the group consisting of hydrogen, fluorine, chlorine, bromine, iodine, alkyl, halosubstituted alkyl, and aryl, with the proviso that at least one Y substituent at a meta position is hydrogen. In the above formula, the preferred alkyl groups represented by Y are those of one to six carbon atoms and the preferred haloalkyl groups are chloroalkyl and bromoalkyl of one to six carbon atoms, and most preferably trichloromethyl or tribromomethyl. The preferred aryl substituents are phenyl or substituted phenyl wherein electron-withdrawing substituents, such as nitro- or trihalomethyl, are present on the ring.

The process is carried out by addition of the benzotrihalide to oleum. The co-products prepared in this manner are benzoyl halides and meta-halosulfonylbenzoyl halides characterized, respectively by the formulas:

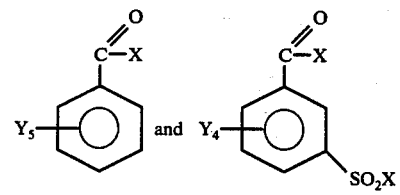

wherein Y is as defined herein above.

DESCRIPTION OF PREFERRED EMBODIMENTS

The preferred benzotrihalide starting materials are benzotrichloride compounds characterized by the formula:

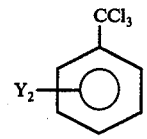

wherein Y is chlorine or hydrogen, especially benzotrichloride and o-chloro-, m-chloro-, and p-chlorobenzotrichloride. These compounds are reacted with oleum, in accordance with the process of this invention, to prepare correspondingly substituted benzoyl chlorides and m-chlorosulfonylbenzoyl chlorides. Thus, when benzotrichloride is employed as the starting material, the co-products obtained by the process of this invention will be benzoyl chloride and m-chlorosulfonylbenzoyl chloride. Utilizing p-chlorobenzotrichloride as the starting material results in the co-production of p-chloro-benzoyl chloride and 4-chloro-3-chlorosulfonylbenzoyl chloride. Starting with m-chlorobenzotrichloride yields, as co-products, m-chloro-benzoyl chloride and 5-chloro-3-chlorosulfonylbenzoyl chloride.

The use of oleum as a sulfonating agent in the process of this invention provides specific advantages in terms of the high yield of meta-isomer obtained in the halosulfonylbenzoyl halide product and, in addition, provides an advantageous degree of control over the proportional yield of the co-products obtained. It has been found that the proportional yield of co-products may be predictably varied, depending on the composition of the oleum reactant. Oleum, a mixture containing sulfur trioxide and anhydrous sulfuric acid, is available in various compositions, depending on the sulfur trioxide content, and may be employed as a sulfonating agent in accordance with this invention, in concentrations as high as 75% or higher. The common commercially available oleum compositions are those containing about 20, 40, 50 and 65 percent sulfur trioxide. The physical properties, such as specific gravity and melting point of oleum compositions vary according to the percent sulfur trioxide present. For example, 20 percent oleum has a melting point of about $-10°$ Celsius and 65 percent oleum has a melting point of about 0° Celsius while an intermediate composition of 45 percent oleum melts at about 35° Celsius. The most preferred oleum compositions for use as sulfonating agents in the process of this invention are those having about 18 to about 70 percent sulfur trioxide, and most preferably oleum compositions having a melting point below ambient temperature.

It has been found that when benzotrihalide is sulfonated in accordance with this invention, the use of oleum of lower strength, such as about 18 to about 25 percent sulfur trioxide will result in increased proportion of benzoyl halide produced whereas the use of oleum of higher strength, such as 65% sulfur trioxide, will result in an increase in the proportion of halosulfonylbenzoyl halide produced. The advantage of such controllable variation of co-products resides in the ease with which the process may be varied to increase or decrease the proportional yield of either co-product, depending on market needs, economic factors or other considerations prevailing at any given time. In a preferred embodiment of the invention, where it is desired to maximize the production of halosulfonylbenzoyl halide and especially the meta-isomer thereof, it is preferred to employ an oleum composition of about 55 to about 70 percent sulfur trioxide.

The temperature at which the process of this invention may be carried out, under atmospheric conditions, may vary considerably, for example from temperatures as low as about 20° or lower to as high as 200° Celsius or higher. Even lower temperatures may be employed, for example, as low as the $-10°$ Celsius (the approximate freezing point of 20% oleum). However, such lower temperatures provide no advantage and thus are not preferred. Similarly, higher temperatures, such as above about 200° Celsius are not preferred since it has been found that an increase in undesirable residues occurs.

The most preferred temperature at which the present process is carried out is from about 10° Celsius of the temperature at which sulfur trioxide distills out of the reaction mixture up to the refluxing temperature. The temperature at which sulfur trioxide will distill out of the reaction mixture will increase as the percentage of sulfur trioxide in the oleum decreases. Thus, the preferred starting temperature will vary depending on strength of the oleum composition employed. Furthermore, as the sulfonation reaction progresses and sulfur trioxide is consumed it is preferred to increase the temperature of the reaction mixture accordingly.

In an alternative embodiment, the content of sulfur trioxide may be maintained at a desired level by continuous or periodic addition of sulfur trioxide to the oleum reaction mixtures as the reaction progresses.

In a preferred mode, using 65 percent oleum as the sulfonating agent, and adding benzotrichloride thereto, the sulfonating agent is initially maintained at below about 60° and preferably at about 20° to about 50° Celsius. As additional benzotrichloride reactant is added and the reaction progresses, depleting the amount of sulfur trioxide present, the temperature is gradually increased, either continuously, or in stages, to a preferred maximum temperature in the later stages of reaction, as the sulfonating agent is consumed to about 140° to about 170° Celsius. It has been found that the reaction initially proceeds exothermically as the sulfur trioxide content of the oleum decreases. Thereafter, HCl is evolved, the reaction becomes endothermic and heat input to the reaction mixture may be increased accordingly.

When a lower strength oleum, such as 20 percent oleum is employed, higher starting temperatures, such as about 80° to 110° Celsius are preferred, with an increase to about 140° to about 170° Celsius in the later stages of reaction, as the sulfonating agent is consumed.

The temperature considerations suggested are premised on the basis of a reaction at about atmospheric pressure. Sub-atmospheric pressures may be employed but are not preferred. Super-atmospheric pressures may be employed with appropriate changes in preferred temperatures in accordance with the vapor pressure changes resulting from such pressure increase.

It has been found particularly advantageous to carry out the process of this invention by the gradual addition of the benzotrihalide to the oleum sulfonating agent and proceeding in this manner as the sulfonating agent is consumed. The gradual addition of the benzotrihalide may be continuous or intermittant. Utilizing this order of addition, it has been found that undesirable side reactions may be substantially avoided. In addition, the reaction may be continued in this manner until substantially all of the sulfonating agent and any water formed is consumed. In practice, an excess of benzotrihalide may be added, thus allowing substantially complete utilization of the sulfonating agent.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celcius.

EXAMPLE I

A reaction vessel, equipped with a reflux condenser, thermometer, external temperature control means, and stirring means, was charged with 46.9 parts of 20% oleum and heated to about 100° C. A total of 195.48 parts of benzotrichloride was added slowly over a period of 3.2 hours. During that time the reaction temperature rose initially to about 115° C. Then, with additional external heat the temperature was gradually raised to about 140° C and maintained thereat for an additional 2.5 hours following the addition of the benzotrichloride. Simple distillation of the reaction product yielded 84.2 parts of a first fraction containing about 70% benzoyl chloride and about 30% unreacted BTC, and a second fraction consisting of 92.6 parts of m-chlorosulfonylbenzoyl chloride. Analysis of the m-chlorosulfonylbenzoyl chloride product indicated approximately 95.8% meta-isomer; 0.1% ortho-isomer; and 4.0% para-isomer.

EXAMPLE II

A reaction vessel was charged with 256.7 parts of 65% oleum and heated to about 46° C. A total of 684.2 parts of benzotrichloride was added slowly to the oleum over a period of 1.5 hours. During the first 30–40% of the addition of the benzotrichloride, the temperature was allowed to rise (with external cooling) to about 100° C. Thereafter the temperature was increased gradually, with external heating, to a maximum of about 150° C during the final stages of benzotrichloride addition and maintained thereat for an additional 2 hours. Separation and analysis of the reaction product yielded 108.9 parts of benzoyl chloride and 577.5 parts m-chlorosulfonylbenzoyl chloride containing 96.1% meta-isomer; 0.1% ortho-isomer; and 3.8% para-isomer.

In a similar manner, following the general procedure of the foregoing examples, substituted benzotrihalides are reacted with oleum to yield substituted benzoyl chlorides and substituted m-halosulfonylbenzoyl halides.

What is claimed is:

1. A process for the co-production of benzoyl halide and meta-halosulfonylbenzoyl halide by the reaction of benzotrihalide with oleum which comprises gradually adding to oleum, a benzotrihalide of the formula:

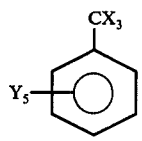

wherein X is bromine or chlorine and Y is individually selected from the group consisting of fluorine, chlorine, bromine, iodine, alkyl, halosubstituted alkyl, aryl, and hydrogen, with the proviso that at least one Y substituent at a meta-position is hydrogen.

2. A process according to claim 1 wherein X is chlorine.

3. A process according to claim 1 wherein the benzotrihalide is characterized by the formula:

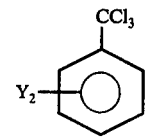

wherein Y is chlorine or hydrogen.

4. A process according to claim 1 wherein the benzotrihalide is benzotrichloride.

5. A process according to claim 1 wherein the oleum is about 18 to about 70 percent sulfur trioxide in sulfuric acid.

6. A process according to claim 5 wherein the reaction is maintained at a temperature of about 20° to about 200° Celsius.

7. A process according to claim 6 wherein the oleum is about 18 to about 25 percent sulfur trioxide in sulfuric acid.

8. A process according to claim 6 wherein the oleum is about 55 to about 70 percent sulfur trioxide in sulfuric acid.

9. A process according to claim 6 wherein the reaction is maintained at a temperature within about 10 Celsius degrees of the temperature at which sulfur trioxide distills out of the oleum.

10. A process for the production of benzoyl chloride and m-chlorosulfonylbenzoyl chloride by the reaction of benzotrichloride with oleum, which comprises gradually adding the benzotrichloride to an oleum reaction medium having an initial composition of about 18 to about 25 percent of sulfur trioxide based on the weight of sulfuric acid, the reaction medium being initially at a temperature of about 80° to about 110° Celsius and gradually increasing to about 140° to about 170° Celsius as the reaction progresses.

11. A process for the production of m-chlorosulfonylbenzoyl chloride and benzoyl chloride by the reaction of benzotrichloride with oleum which comprises gradually adding the benzotrichloride to an oleum reaction medium having an initial composition of about 55 to about 70 percent sulfur trioxide, based on the weight of sulfuric acid, the reaction medium being initially at a temperature of below about 60° Celsius and gradually increasing to about 140° to about 170° Celsius as the reaction progresses.

* * * * *